US00PP14799P3

(12) United States Plant Patent
Westhoff

(10) Patent No.: US PP14,799 P3
(45) Date of Patent: May 18, 2004

(54) VARIETY OF SANVITALIA PLANT NAMED 'WESSASTAR'

(50) Latin Name: *Sanvitalia speciosa*
Varietal Denomination: Wessastar

(75) Inventor: Heinrich Westhoff, Fresenhorst 22-24, 46354 Südlohn/Oeding (DE)

(73) Assignees: Heinrich Westhoff, Sudlohn/Oeding (DE); Josef Westhoff, Sudlohn/Oeding (DE)

( * ) Notice: Subject to any disclaimer, the term of this patent is extended or adjusted under 35 U.S.C. 154(b) by 4 days.

(21) Appl. No.: 10/101,105

(22) Filed: Mar. 19, 2002

(65) Prior Publication Data

US 2003/0182699 P1 Sep. 25, 2003

(51) Int. Cl.[7] ..... A01H 5/00
(52) U.S. Cl. ..... Plt./263
(58) Field of Search ..... Plt./263

*Primary Examiner*—Howard J. Locker
(74) *Attorney, Agent, or Firm*—Webb Ziesenheim Logsdon Orkin & Hanson, P.C.

(57) ABSTRACT

A new and distinct early flowering Sanvitalia plant with intense yellow-orange colored flowers and vigorous, compact growth.

2 Drawing Sheets

Varietal denomination: *Sanvitalia speciosa.*
Classification: 'Wessastar'.

BACKGROUND OF THE INVENTION

The present invention comprises a new and distinct cultivar of Sanvitalia plant known by the varietal name 'Wessastar'. The new variety was discovered in 1999 in a selected breeding program in Südlohn, Germany. The new variety is a selection from the cross of proprietary unpatented breeding plants named 98 Sa 17 (female) and 98 Sa 07 (male). The growth character, flower color, and foliage color of the new variety is similar to its parents but with smaller diameter flowers and shorter internodes. The new variety was first asexually reproduced in February 1999 by cuttings in Südlohn, Germany. The new variety has been trial and field tested at Südlohn and has been found to retain its distinctive characteristics and remain true to type through successive propagations.

The following traits in combination distinguish 'Wessastar' as a new and distinct cultivar:

1. Large flower diameter.
2. Compact growth.
3. Many flowers.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
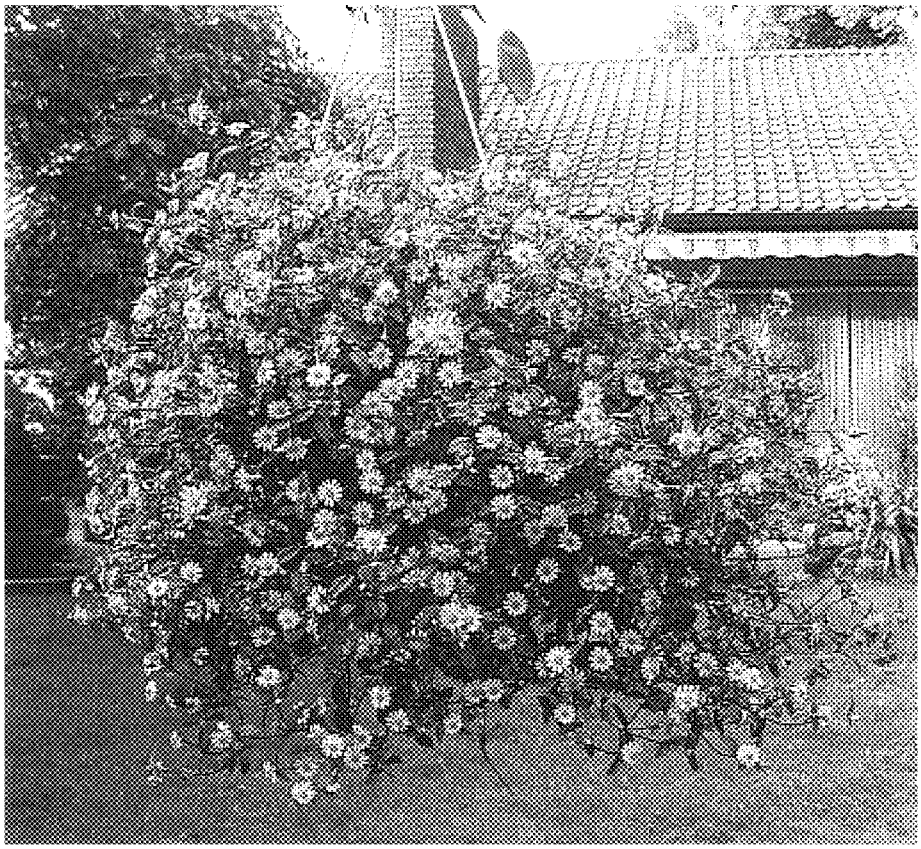
FIG. 1 is a picture of the hanging plant.
Figure 2:
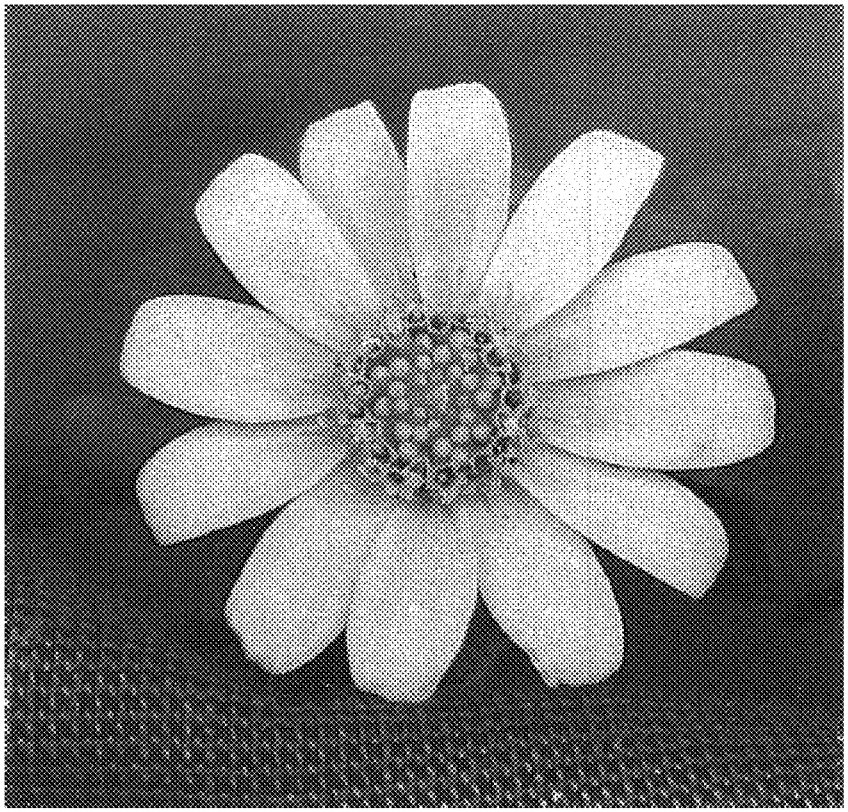
FIG. 2 is a close-up of the flower.

The following detailed description sets forth characteristics of the new cultivar. The data which defines these characteristics were collected by asexual reproductions via terminal cuttings and tissue culture carried out in Südlohn, Germany. Plants for the description were 20 weeks old, grown in an outside greenhouse at 20–25° C. daytime temperature and 16–18° C. night temperature with long day light levels of 3,000–50,000 lux. The color readings were taken on a plant outdoors and in a greenhouse under natural light. Color references are primarily to The R.H.S. Colour Chart of The Royal Horticultural Society of London.

'Wessastar' compares to 'Aztekengold' (unpatented) as follows:

| Similarities | Differences |
|---|---|
| Leaf form. | Flower diameter of 'Wessastar' is bigger. |
| Leaf color. | Sepals of 'Wessastar' are bigger. |
| Flower color. | Internodes of 'Wessastar' are shorter. |

'Wessastar' compares to 'Sunbini' (unpatented) as follows:

| Similarities | Differences |
|---|---|
| Leaf form. | Flower diameter of 'Wessastar' is bigger. |
| Leaf color. | Flower color of 'Wessastar' is more orange-yellow. |
| Sepal color. | Sepals of 'Wessastar' are bigger. |

PLANT

Form: Spreading.
Height: 16–20 cm from soil to top of flowers; 40 cm wide.
Growth: Vigorous.
Time to produce a finished flowering plant from a rooted cutting: About 12 weeks in a 12 cm container.
Branching habit: Well branched, nearly at every node.
Roots:
*Habit.*—Vigorous, fine, well-branched.
*Time to initiate roots.*—About 16 days at 18° C.
*Time to develop roots.*—About 26 days at 18° C.
Lateral branches:
*Color.*—144B and 166A and 166B.
*Texture.*—Smooth, slightly pubescent.

*Diameter.*—Main branches: 2.7 mm. Lateral branches: 1.5 mm.
*Internode length.*—4 cm.

Foliage:
*Arrangement.*—Opposite; decussate; no petioles.
*Size of leaf.*—Length: 2.4 cm. Width: 1.3 cm.
*Shape of leaf.*—Ovate to elliptic.
*Shape of apex.*—Acute; slightly rounded.
*Shape of base.*—Cordate.
*Texture.*—Leathery; setiform pubescent.
*Aspect.*—Flat to slightly cupped.
*Margin type.*—Entire.
*Color.*—Young leaves: Upper surface: 147A. Lower surface: 147B. Mature leaves: Upper surface: 147A. Lower surface: 147C.
*Veins.*—Venation type: Pinnate. Color: Upper surface: 144B. Lower surface: 147B.

FLOWER

Bud (at early stage of development):
*Shape.*—Lenticular.
Length.—4.1 mm.
*Diameter.*—5.8 mm.
*Color.*—137A.

Natural flowering season: April or May until end of October.

Lastingness of an individual bloom on the plant: Average of 25–28 days depending on the weather/season.

Flower type and habit: Composite.

Ray florets:
*Number.*—12.
*Length.*—6.6 mm.
*Width.*—3.2 mm.
*Shape.*—Oblong; semi-rectangular.
*Aspect.*—Flat.
*Margin.*—Entire.
*Texture and appearance.*—Smooth, satiny.
*Color when just opening.*—Upper surface: 17A. Lower surface: 144B and 151A.
*Color when fully opened.*—Upper surface: 14A. Lower surface: 12B with stripes of 145A.
*Disc florets.*—Number per inflorescence: 90–100. Color: Young: 144A. Mature: 153B. Diameter: 6.0–6.5 mm.

Sepals:
*Shape.*—Nearly round to cordate.
*Margin.*—Entire.
*Texture.*—Smooth.
*Number.*—5.
*Color.*—Upper surface: 146A and 146B. Lower surface: 146A and 146B.

REPRODUCTIVE ORGANS

Androecium:
*Presence.*—On disc florets only.
*Number.*—One stamen per disc floret.
*Filament length.*—2.1 mm.
*Anthers.*—Shape: Oblong. Length: 1.0 mm. Width: 0.2 mm. Color: 17B.

Pollen:
*Color.*—17C.
*Amount.*—Moderate.

Gynoecium:
*Presence.*—On ray florets only.
*Pistils.*—Number: Two pistils per ray floret. Length: 3.1 mm. Style: Length: 1.0 mm. Color: 17D. Stigma: Shape: Two thread-like filaments per ray floret. Color: 17B.
*Seeds.*—Form: Ovate to reniform. Length: 2.0 mm. Width: 1.6 mm. Diameter (thickness) 0.6–0.9 mm. Color: 195A and 195B.

GENERAL

Fragrance: None.

Disease/pest resistance: High disease resistance.

Weather tolerance: Blooming occurs until frost, but no winter hardiness. The new variety is very resistant to wind and rain.

I claim:

1. A new and distinct variety of Sanvitalia plant substantially as shown and described.

* * * * *